US008974441B2

(12) United States Patent
Oskin et al.

(10) Patent No.: US 8,974,441 B2
(45) Date of Patent: Mar. 10, 2015

(54) ADJUSTABLE DEVICE HANDLE AND RELATED METHODS OF USE

(71) Applicants: Christopher L. Oskin, Grafton, MA (US); William M. Asselin, Lunenburg, MA (US)

(72) Inventors: Christopher L. Oskin, Grafton, MA (US); William M. Asselin, Lunenburg, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/745,057

(22) Filed: Jan. 18, 2013

(65) Prior Publication Data
US 2013/0184691 A1    Jul. 18, 2013

Related U.S. Application Data

(60) Provisional application No. 61/587,897, filed on Jan. 18, 2012.

(51) Int. Cl.
*A61B 17/00* (2006.01)
*A61B 1/00* (2006.01)
*A61B 1/005* (2006.01)
*A61B 1/018* (2006.01)

(52) U.S. Cl.
CPC ....... *A61B 17/00234* (2013.01); *A61B 1/00066* (2013.01); *A61B 1/00121* (2013.01); *A61B 1/00128* (2013.01); *A61B 1/0014* (2013.01); *A61B 1/0052* (2013.01); *A61B 1/018* (2013.01)
USPC ............................................. 606/1; 600/101

(58) Field of Classification Search
CPC ............... A61B 19/22; A61B 19/2203; A61B 2014/2242; A61B 1/041; A61B 1/00016
USPC ............................................. 606/1; 600/101
See application file for complete search history.

(56) References Cited

U.S. PATENT DOCUMENTS

| | | | |
|---|---|---|---|
| 4,254,762 A * | 3/1981 | Yoon | 600/114 |
| 6,190,360 B1 * | 2/2001 | Iancea et al. | 604/164.09 |
| 6,969,373 B2 * | 11/2005 | Schwartz et al. | 604/170.03 |
| 2004/0068253 A1 * | 4/2004 | Bayer et al. | 606/1 |
| 2006/0252993 A1 | 11/2006 | Freed et al. | |
| 2009/0088600 A1 * | 4/2009 | Meloul | 600/104 |
| 2009/0124858 A1 * | 5/2009 | Oskin et al. | 600/156 |
| 2010/0063354 A1 * | 3/2010 | Hashimoto et al. | 600/106 |

FOREIGN PATENT DOCUMENTS

WO    WO 2011/150111 A1    12/2011

OTHER PUBLICATIONS

International Search Report for International Application No. PCT/US2013/022149, mailed Apr. 23, 2013, 2 pgs.

* cited by examiner

*Primary Examiner* — William Thomson
*Assistant Examiner* — Sebastian X Lukjan
(74) *Attorney, Agent, or Firm* — Bookoff McAndrews, PLLC

(57) ABSTRACT

An adjustable accessory for a medical device having an elongate tube and a lumen extending therein, the adjustable accessory including a handle adapted for connection to a proximal end of the elongate tube. The handle including a longitudinal axis and a slot on the handle transverse to the longitudinal axis. The slot includes multiple detent positions and a fitting movably disposed in the slot. The fitting is configured to be releasably secured within one of the detent positions, and the fitting includes a port in communication with the lumen of the elongate tube.

20 Claims, 3 Drawing Sheets

ADJUSTABLE DEVICE HANDLE AND RELATED METHODS OF USE

CROSS-REFERENCE TO RELATED APPLICATIONS

This application claims the benefit of priority of U.S. Provisional Application No. 61/587,897, filed Jan. 18, 2012, which is incorporated by reference herein in its entirety.

FIELD OF THE DISCLOSURE

Embodiments of the present disclosure relate generally to medical devices suitable for providing access to internal body structures during medical procedures. In particular, embodiments of the instant disclosure relate to the usability of such medical devices.

BACKGROUND

More than 90% of the human population is right-handed. As a result, medical and surgical equipment in use today, such as endoscopes and other endoscopic or minimally invasive surgical equipment, are asymmetrical, designed largely for right-handed operators.

Conventionally, devices such as, e.g., endoscopic devices, include handles designed for a right-handed person to operate the device efficiently and effectively. That design causes significant difficulty when a left-handed person tries to maneuver the device. In particular, manipulating a right-handed device is awkward for a left-handed person, and a left-handed operator encounters difficulty in seeing what she is doing, as visibility factors are significantly different from the left and right sides of the device. Similarly, a right-handed operator may have difficulty using an instrument designed for a left-handed operator. These factors produce both discomfort and inefficient usage. Difficulties may be aggravated during surgical procedures that require precise and careful tool movement inside the body. Additional problems include an inability to steady the tool, as well as difficulty reaching certain actuator switches that may also result.

Existing solutions to this problem include endoscopic devices with separate handles for left and right-handed operators. Hospitals often employ disposable endoscopic devices in an effort to minimize the risk of cross-contamination and hospital-acquired infection, however, and maintaining an inventory of two different handle configuration for each type of endoscopic device would be an expensive proposition. Further, some surgical procedures require two operators, and in such cases, different handedness of operators can lead to significant time delay and possible risk to successful conclusion of a procedure. In such scenarios, endoscopic devices with separate handles provide an impractical solution.

Therefore, there exists a need for an inexpensive and adjustable handle configuration, which allows both left-handed and right-handed users to customize the device for comfortable use.

SUMMARY

Embodiments of the disclosure provide an adjustable medical device handle.

In accordance with an aspect of the present disclosure an adjustable accessory for a medical device may include an elongate tube and a lumen extending therein. The adjustable accessory may include a handle adapted for connection to a proximal end of the elongate tube. The handle may further include a longitudinal axis and a slot defined by a portion of the handle, with the slot extending generally transverse to the longitudinal axis. Additionally, the slot may include a plurality of detent positions and a fitting movably disposed in the slot and configured to be releasably secured within one of the multiple detent positions, the fitting may further include a port in communication with the lumen of the elongate tube.

In various embodiments, the accessory may further include one or more of the following aspects: a portion of the slot may be in communication with the lumen; an entirety of the slot may be in communication with the lumen; a distal end of the handle may include geometric structures for attachment with the elongate tube; the fitting may include multiple ports converging at a single channel; the slot may include a sealing mechanism configured to prevent fluid ingress into the handle; the fitting may include a luer-lock connector; the fitting and the slot may be detachably connected; and the fitting may include a plurality of ports.

In accordance with another aspect of the disclosure, an adjustable medical device may include an elongate member having a proximal end, a distal end, and a lumen extending between the proximal end and the distal end, the lumen defining one or more working channels. A handle may be adapted for connection to the proximal end of the elongate member. The handle may include a longitudinal axis and a slot formed generally transversely to the longitudinal axis, the slot may be in communication with the working channel, and the slot may include a plurality of detent positions formed therein. A fitting may be movably disposed within the slot and further adapted for selective engagement in at least one detent position. In addition, the fitting may include two or more ports configured to provide access to the working channel.

In various embodiments, the adjustable medical device may further include one or more of the following: the fitting may include multiple lumens corresponding to the ports; the fitting may be removably coupled to the slot; the slot may have an arcuate geometry; the at least one detent position may include threads for coupling to the fitting; the slot may include a sealing mechanism configured to prevent fluid ingress into the handle; and the fitting may include a luer-lock connector.

In accordance with an alternate aspect of the disclosure, a method of using an adjustable medical device is disclosed. The medical device may include an endoscopic access sheath having a handle and an elongate tube having a lumen therein. The handle may further include a port in communication with the lumen and the port may be movably disposed in a slot of the handle. In addition, the method may include moving the port from a first position within the slot to a second position within the slot and inserting a medical device through the port into the lumen of the elongate member.

In various embodiments, the method may further include one or more of the following aspects: the port and lumen may be detachably connected; the port may include a luer-lock connector; and the port may include a sealing mechanism configured to prevent fluid ingress into the handle.

Additional objects and advantages of the disclosure will be set forth in part in the description, which follows, and in part will be evident from the description, or may be learned by practice of the disclosed subject matter. The objects and advantages of the disclosed subject matter will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodi

DESCRIPTION OF THE EMBODIMENTS

Reference will now be made in detail to embodiments of the disclosure, as illustrated in the accompanying drawings. Wherever possible like reference numbers will be used throughout the drawings to refer to the same or like parts.

Overview

Embodiments of the present disclosure relate to an adjustable handle and related methods for use in a device with, e.g., working channels for advancing tools to an operation site. Such handles may also be used with any endoscopic device, including access sheaths and surgical tools. An adjustable handle includes a transverse slot formed in the handle, the slot opening to the working channel. The slot includes two or more detent positions, and a fitting is adapted to be selectively seated in one or the other of the detent positions. The fitting may include separate ports for left-handed and right-handed users to connect the fitting with the working channel. Alternatively, users may select the appropriate detent position according to their handedness. The fitting may include a luer-lock connector. However, any suitable fitting known in the art may be used.

In addition, while the discussion of systems and methods below may generally refer to endoscopic devices as illustrative examples, the described designs can be used in any device having a handle nominally designed for specifically for a right-handed or left-handed operator. It will thus be understood that the description below sets out designs for an adjustable endoscopic device, applying to a wide range of medical devices, such as, laparoscopes.

Exemplary Embodiments

Figure 1A:
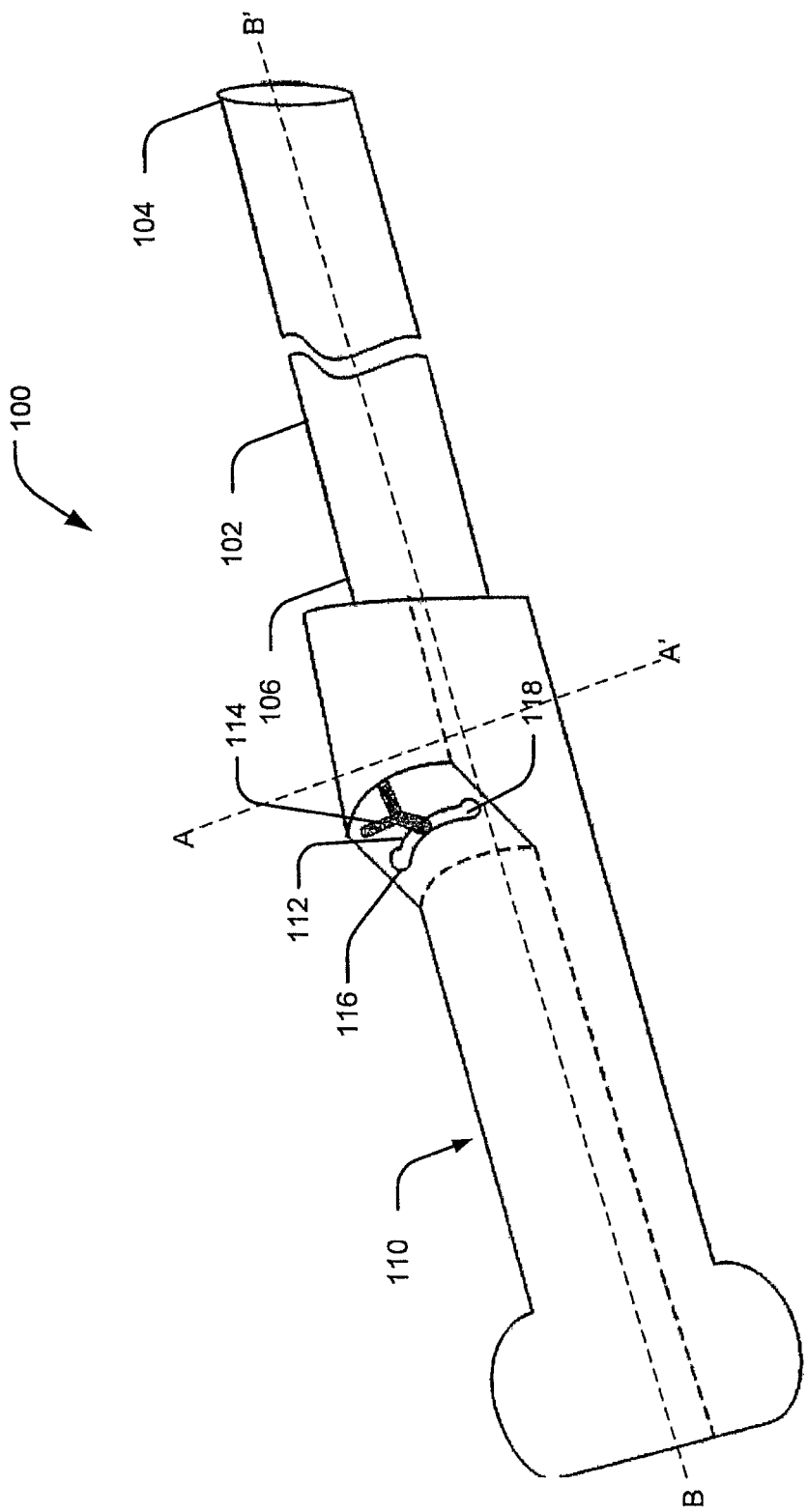
- FIGS. 1A and 1B illustrate an adjustable endoscopic device, according to an embodiment of the present disclosure.
Figure 1B:
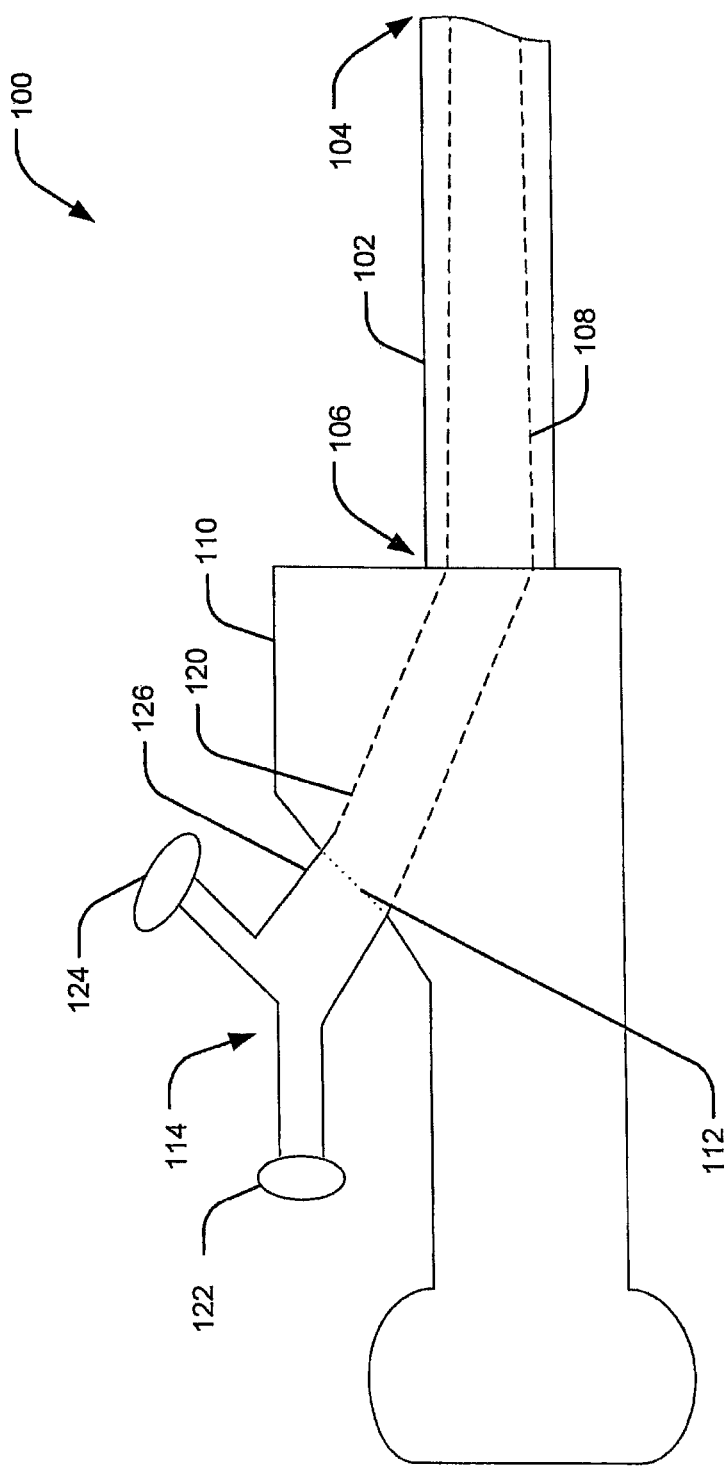

FIGS. 1A and 1B illustrate an exemplary adjustable endoscopic device 100. Particularly, FIG. 1A presents a side view of the endoscopic device 100, and FIG. 1B is a cross-sectional view of the endoscopic device 100 taken along plane B-B'. The endoscopic device 100 may be a conventional endoscopic device that includes an elongate tube 102 having a distal end 104, a proximal end 106, and one or more working channels 108 extending from the distal to proximal end. Proximal end 106 may be coupled to a handle 110, while distal end 104 remains open to allow one or more devices, such as snares, biopsy forces, scissors, and/or laser fibers, to extend towards a surgical site through the working channel 108. Elongate tube 102 is a well-known endoscopic device tube, with working channels having a cross-sectional configuration adapted according to the operating environment. Handle 110 disclosed in the present disclosure includes a slot 112 having openings 116, 118 and a fitting 114 adapted to be seated in the slot, allowing a left or right handed user to adjust the position of fitting 114 to facilitate convenient operation of endoscopic device 100.

In some respects, handle 110 is substantially similar to a conventional endoscopic device handle. For example, handle 110 is connected to the proximal end 106 of elongate tube 102, and it is a substantially cylindrical structure designed to be held in a user's hand. Handle 110's proximal portion may include design features, such as finger grooves to assist in endoscopic device handling. Its cross-section may be uniform or may taper toward the distal end 104. In addition, handle 110 may include a number of ports connected to the device's working channels, and any number of actuators.

In some embodiments, the handle 110 may be detachable from the elongate tube 102 for sterilization purposes. Further, in endoscopic devices with multiple working channels, handle 110's distal end may be configured for attachment to a number of conventional endoscopic access sheaths, employing known means for adjusting to accommodate various sheath sizes. To allow efficient and fast attachment of the handle with the elongate tube, handle 110's distal end and elongate tube's proximal end may include geometric structures, for example, latching pins, keys, and keyways, to ensure precise rotational orientation of the working channels and lumens. As would be understood by a person skilled in the art, any other suitable attachment means may be employed.

As shown in FIG. 1A, slot 112 is formed transversely in an upper surface of handle 110, culminating in two detent positions 116, 118. Detent positions 116, 118 are located so that one is particularly suitable for a left-handed user and one for a right-handed user. The entirety of slot 112, including each detent positions 116, 118, may be in communication with a channel 120, which in turn is in communication with one or more working channels 108 of the device 100. Channel 120 may be formed within the handle body, or if the handle body is hollow, channel 120 may be a flexible lumen adapted to move transversely between the detent positions 116, 118 to direct an incoming medical device toward the working channel 108. As will be clear from the following discussion, the length of slot 112 and the location of detent positions 116, 118 are determined according to the most comfortable locations for operating in operation by right-handed and left-handed operators. Slot 112 along with the detent positions 116, 118 are discussed in detail in the following section in connection with FIGS. 2 and 3.

Fitting 114 is carried in slot 112, and it provides an entrance port for a medical device being used in conjunction with the working channel 108. The fitting may be a coupling having one or more ports configured to allow insertion of suitable medical devices. In one embodiment of the present disclosure, fitting 114 takes the form of a well-known detent fitting having open and closed positions, the device being biased to the closed position using mechanisms such as an internal spring. In the closed position, the fitting 114 fits exactly into one of the detent positions 116, 118. When fitting 114 is extended (simply by pulling on the end of the fitting 114) into the open position, fitting 114 can slide transversely in slot 112 between the detent positions 116, 118. In that manner, the operator can move fitting 114 between left-handed and right-handed operating positions. Operation and structure of detent position and fitting are sufficiently familiar to those in the art that no further details are required here.

Various attachment mechanisms may allow movement of fitting 114 between the closed and open positions. For example, an engagement mechanism can be built into the handle itself. In one embodiment, a Luer-lock connector may allow mating between fitting 114 and detent positions 116, 118. To this end, the distal end of fitting or the slot surface may be threaded. In an alternate embodiment, magnetic attachment, interference fit, or other known methods may allow a detachable connection between the fitting 114 and detent positions 116, 118.

In addition, a number of alternative fitting structures are available to the art. For example, the various dimensions could be arranged so that the medical device is movable within the slot, and a simple cylindrical fitting could be provided having practically the same dimension as that of the detent positions 116, 118. With that structure, the fitting 114 can simply be pressed into the desired detent position. When a change of position is desired, the fitting is simply pulled out, moved to the other detent position, and pressed into that location. Alternatively, the fitting may be dimensioned so that its outer diameter is greater than the width of slot 112 such that the fitting can be retained within a selected detent position. When the fitting is transferred to the open position, the diameter of the fitting portion exposed to the slot may be sufficiently small so that the fitting can slide transversely in slot 112. Other arrangements will be clear to those in the art.

As depicted in FIG. 1B, fitting 114 includes two hollow ports 122 and 124 at its proximal end, one for right-handed and the other one for left-handed users. As depicted, the ports 122,124 converge at the distal end of fitting 114 as a hollow lumen 126 adapted to be seated into the detent positions 116, 118. In some embodiments, fitting 114 may include lumens 126 corresponding to each port of fitting 114, the lumens, which may communicate individually with multiple working channels of the endoscopic access device. Further, the proximal ends of ports 122, 124 diverge such that an unhindered view is provided to both left-handed and right-handed users. In some embodiments, the use of multiple medical devices may necessitate fitting with multiple ports. Alternatively, the ports 122, 124 may be rotatable about lumen 126 of the fitting 114 to fine-tune the port orientation. In another variation, ports 122, 124 could be formed of a flexible material, allowing each port to be aligned as required with an inserted device, As shown, ports 122, 124 diverge from the lumen 126 as two separate channels to provide openings for inserting tools into the working channel 108 via lumen 126. In general, fitting 114 carries port 122, which may allow a left-handed user to insert a tool conveniently, once the fitting lies in a desired detent position. Similarly, a right hand user may insert tools using port 124. It should be understood that left-handed and right-handed users may interchangeably employ ports 122 and 124. In an alternate embodiment, fitting 114 may include a single hollow port that may swivel in any desired direction. Ports 122, 124 may be manufactured as flexible channels, allowing better port orientation according to user preference.

In an alternative embodiment, a transparent member, such as, a flexible plastic sheet may be wrapped around at least a portion of handle 110, providing a barrier against the ingress of body fluids and materials. The transparent member may be suitably dimensioned to cover handle 110 completely, and its dimensions may vary according to handle 110 configurations. It should be understood that this member does not cover the openings on the ports 122, 124, thus allowing tool insertion. In an alternate embodiment, the transparent member may cover either upper or lower surface of handle 110 selectively. Alternatively, the slot 112 may include a sealing device, for example, a rubber gasket surrounding the detent positions 116, 118 through which the fitting 114 may protrude. The gasket may prevent fluid ingress in the handle 110 during surgical tool removal from ports 122, 124.

Handle 110 and its associated components may be formed from any suitable moldable material with sufficient rigidity to be actuated by a user. Suitable materials may include synthetic plastics and polymers. Alternatively, metals, such as stainless steel, may also be suitable for such applications.

Figure 2:
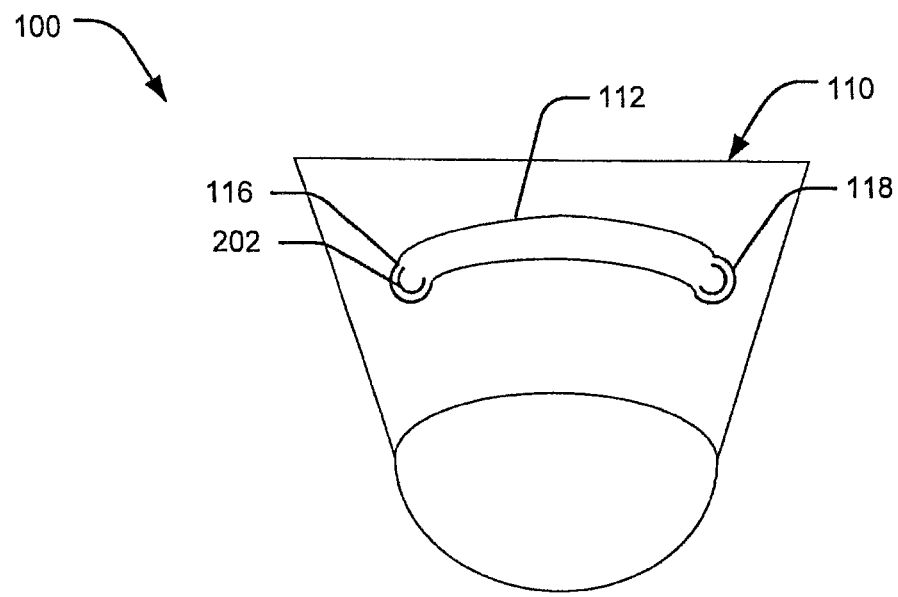
FIG. 2 presents a cross-sectional view of the endoscopic device taken along plane A-A' shown in FIG. 1A.

FIG. 2 presents a cross-sectional view of the endoscopic device taken along plane A-A'. The illustrated embodiment shows handle 110 having slot 112 extending transversely with separate detent positions 116, 118 for left-handed and right-handed users, respectively. Further, detent positions 116, 118 engage fitting 114, allowing a user to insert tools within the endoscopic device conveniently.

As shown, slot 112 includes a generally arcuate configuration, with the two ends of the slots leading to two semi-circular detent positions 116, 118. Alternatively, slot 112 may be rectangular. The width of the slot 112 may vary based on the required locations for detent positions 116, 118. It should be understood that some left-handed users may prefer fitting 114, having inlet ports, being positioned substantially towards the left side of handle 110. On the other hand, a right-handed user may desire inserting a tool from a position close to the top end of the handle. Consequently, two detent positions 116, 118 may be the positioned based on user's handedness. Further, the illustrated embodiment shows the detent positions 116, 118 being the extreme positions of slot 112. It should be understood that fitting 114 might be locked at any desired position towards the left or right side of slot using known attachment mechanisms. Moreover, the cross-sectional configurations of slot and detent positions may be uniform or irregular. The ports 122, 124 and detent positions 116, 118 may have any suitable cross-section based on the configuration of incoming tools or working channel's 108 configuration.

To engage fitting 114, detent positions 116, 118 may include geometrical structures that allow locking fitting 114 in its closed position. As shown, the inner surface of the detent positions 116, 118 may include a half-threaded configuration 202 to allow Luer-lock connection between the two devices. Other attachment mechanisms may be contemplated. For example, detent positions 116, 118 may include projections, magnets, or other known detachable mechanisms known to those in the art. Alternatively, the detent positions 116, 118 and the fitting 114 may fit together smoothly.

For performing an endoscopic surgery employing an embodiment of the present disclosure, a user first selects a detent position 116 or 118 on handle 110, according to his or her preference. To achieve the closed position of fitting 114 at the desired detent position, the user loosens fitting 114 by pulling it or unscrewing, for example. Subsequently, fitting 114 is moved to the selected detent position. In embodiments where channel 120 is moved with fitting 114, channel 120 along with the fitting is locked in the selected detent position on the slot 112 by pushing or screwing. In an embodiment, fitting 114 may connect to a spring or a magnet that may push loosened fitting 114 to the closest detent position. Once the fitting 114 is aligned according to a user's preference, the user inserts required tools through port 122 or 124 extending from the distal end of elongate tube via working channel 108. Subsequently, the user can perform the required procedure at the surgical site.

Figure 3:
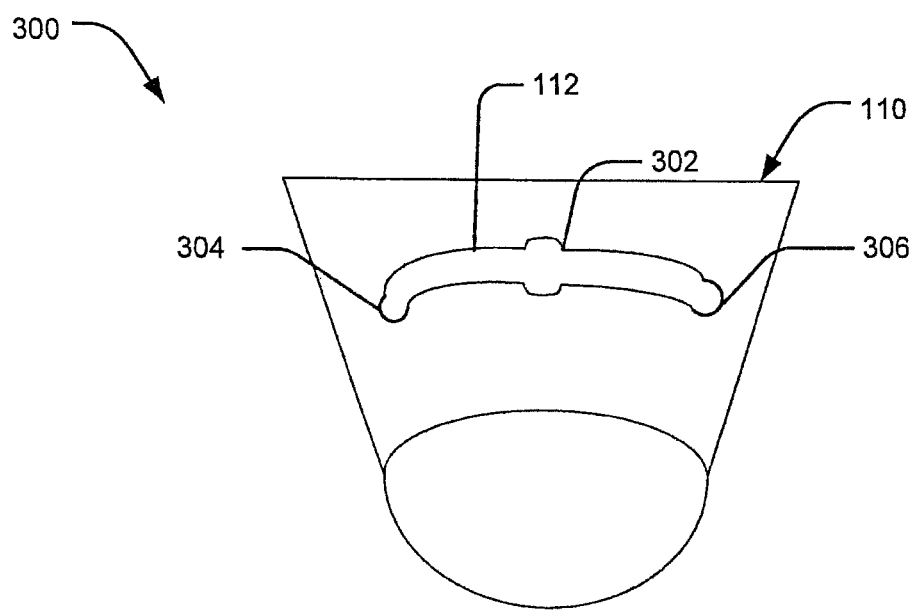
FIG. 3 illustrates an alternate embodiment of the endoscopic device taken along plane A-A' shown in FIG. 1A.

FIG. 3 depicts an alternate embodiment 300 of the endoscopic device 100 taken along plane A-A' (FIG. 1). The illustrated embodiment shows handle 110 having slot 112 with three separate detent positions namely, a central detent position 302, a left-handed detent position 304, and a right-handed detent position 306. The left-handed and right-handed detent positions 304, 306 are similar to the detent positions 116, 118, shown in FIG. 2. In addition, the illustrated embodiment depicts central detent position 302, utilized for placing the fitting 114 in a neutral position, for example, during endoscopic device shipment, transport, or accommodating user preference. The placement of the three positions 302, 304, 306 may vary based on user's handedness.

Adjustable endoscopic device 100 and related components described above allows both left-handed as well as right-handed users to perform surgical procedures with equal facility. A particular difficulty encountered in the art arises when a surgical procedure requires two users, and those users turn out to be differently handed. In such scenarios, an adjustable handle, such as handle 110, allows each user to reset the handedness of the device, allowing them to conveniently change the ports on handle 110 as described above.

It should be apparent that the device of the present disclosure may be used to carry out a variety of medical or non-medical procedures, including surgical and diagnostic procedures in a wide variety of bodily locations. A number of procedures, such as, mucosal resection or ablation, polyp removal, or similar procedures involving a variety of body organs, such as the esophagus, stomach, bladder, or the urethra can be accomplished using the method described above. In addition, at least certain aspects of the illustrated embodiments may be combined with other aspects of the embodiments, or removed without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. An adjustable accessory for a medical device having an elongate tube and a lumen extending therein, the adjustable accessory comprising:
   a handle adapted for connection to a proximal end of the elongate tube, wherein the handle includes a longitudinal axis, the handle including a slot defined by a portion of the handle, the slot having a length and a width, wherein the length of the slot extends transversely to the longitudinal axis, and wherein the slot includes a plurality of detent positions formed therein; and
   a fitting movably disposed in the slot and configured to be releasably secured within one of the plurality of detent positions,
   wherein the fitting includes a port in communication with the lumen of the elongate tube, and
   wherein the fitting moves relative to the handle.

2. The accessory of claim 1, wherein a portion of the slot is in communication with the lumen.

3. The accessory of claim 1, wherein an entirety of the slot is in communication with the lumen.

4. The accessory of claim 1, wherein a distal end of the handle includes geometric structures for attachment with the elongate tube.

5. The accessory of claim 1, wherein the fitting includes multiple ports converging at a single channel.

6. The accessory of claim 1, wherein the slot includes a sealing mechanism configured to prevent fluid ingress into the handle.

7. The accessory of claim 1, wherein the fitting includes a luer-lock connector.

8. The accessory of claim 1, wherein the fitting and the slot are detachably connected.

9. The accessory of claim 1, wherein the fitting includes a plurality of ports.

10. An adjustable medical device comprising:
    an elongate member having a proximal end, a distal end, and a lumen extending between the proximal end and the distal end, the lumen defining one or more working channels;
    a handle adapted for connection to the proximal end of the elongate member, wherein the handle includes a longitudinal axis and a slot having a length and a width, the length extending transversely to the longitudinal axis, wherein the slot is in communication with the working channel, and the slot includes a plurality of detent positions formed therein; and
    a fitting movably disposed within the slot and further adapted for selective engagement in at least one detent position,
    wherein the fitting includes two or more ports configured to provide access to the working channel, and
    wherein the fitting moves relative to the handle.

11. The adjustable medical device of claim 10, wherein the fitting includes multiple lumens corresponding to the ports.

12. The adjustable medical device of claim 11, wherein the fitting is removably coupled to the slot.

13. The adjustable medical device of claim 10, wherein the slot has an arcuate geometry.

14. The adjustable medical device of claim 10, wherein at least one of the detent positions includes threads for coupling to the fitting.

15. The adjustable medical device of claim 10, wherein the slot includes a sealing mechanism configured to prevent fluid ingress into the handle.

16. The adjustable medical device of claim 10, wherein the fitting includes a luer-lock connector.

17. An adjustable accessory for a medical device having an elongate
    tube and a lumen extending therein, the adjustable accessory comprising:
    a handle adapted for connection to a proximal end of the elongate tube, wherein the handle includes a longitudinal axis, the handle including a slot bounded on all sides by the handle and extending transversely to the longitudinal axis, and wherein the slot includes a plurality of detent positions formed therein; and
    a fitting movably disposed in the slot and configured to be releasably secured within one of the plurality of detent positions,
    wherein the fitting includes a port in communication with the lumen of the elongate tube, and
    wherein the fitting moves relative to the handle.

18. The accessory of claim 1, wherein the slot is disposed at an acute angle relative to the longitudinal axis of the handle.

19. The accessory of claim 1, wherein fitting comprises a proximal end extending in a plane non-parallel to a plane of the handle.

20. The accessory of claim 1, wherein at least two of the detent position are at opposite ends of the slot.

* * * * *